(12) United States Patent
Doyle, III et al.

(10) Patent No.: US 9,907,515 B2
(45) Date of Patent: Mar. 6, 2018

(54) HEALTH MONITORING SYSTEM (71) Applicant: The Regents of the University of California, Oakland, CA (US)

(72) Inventors: Francis J. Doyle, III, Cambridge, MA (US); Eyal Dassau, Cambridge, MA (US); Howard Zissser, Cambridge, MA (US); Rebecca Harvey, Cambridge, MA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/422,811

(22) Filed: Feb. 2, 2017

(65) Prior Publication Data

US 2017/0156682 A1 Jun. 8, 2017

Related U.S. Application Data (63) Continuation of application No. 13/166,806, filed on Jun. 22, 2011.

(60) Provisional application No. 61/357,409, filed on Jun. 22, 2010.

(51) Int. Cl.
 *A61B 5/00* (2006.01)
 *A61B 5/145* (2006.01)
(52) U.S. Cl.
 CPC .......... *A61B 5/746* (2013.01); *A61B 5/14532* (2013.01); *A61B 5/7275* (2013.01)
(58) Field of Classification Search
 None
 See application file for complete search history.

(56) References Cited

U.S. PATENT DOCUMENTS

| 5,660,163 A * | 8/1997 | Schulman | A61B 5/14865 204/403.11 |
| 8,452,359 B2 * | 5/2013 | Rebec | A61B 5/14532 600/310 |
| 8,454,576 B2 * | 6/2013 | Mastrototaro | A61B 5/14532 604/504 |
| 8,622,988 B2 * | 1/2014 | Hayter | A61B 5/0031 604/503 |
| 2002/0161288 A1 | 10/2002 | Shin | |
| 2003/0060692 A1 | 3/2003 | Ruchti | |
| 2008/0033272 A1 | 2/2008 | Gough | |

(Continued)

OTHER PUBLICATIONS

International Search Report and Written Opinion in PCT/US2012/039213.

(Continued)

*Primary Examiner* — Fekadeselassie Girma
(74) *Attorney, Agent, or Firm* — Richard Aron Osman (57) ABSTRACT

A machine for processing continuous glucose monitoring data and issuing an alert if hypoglycemia is imminent has three modules: (a) a pre-processing module that receives and modulates continuous glucose monitoring data by reducing noise and adjusting for missed data points and shifts due to calibration; (b) a core algorithm module that receives data from the pre-processing module and calculates a rate of change to make a hypoglycemia prediction, and determine if hypoglycemia is imminent; and (c) an alarm mode module that receives data from the core algorithm and issues an audio or visual alert or warning message or a negative feedback signal to an insulin delivery device if hypoglycemia is imminent.

5 Claims, 8 Drawing Sheets

(56) References Cited

U.S. PATENT DOCUMENTS

| | | | | |
|---|---|---|---|---|
| 2008/0269714 A1* | 10/2008 | Mastrototaro | ..... | A61B 5/14532 604/504 |
| 2009/0156924 A1 | 6/2009 | Shariati | | |
| 2009/0163781 A1* | 6/2009 | Say | ..... | A61M 5/1723 600/301 |
| 2009/0105573 A1 | 8/2009 | Malecha | | |
| 2010/0057042 A1* | 3/2010 | Hayter | ..... | A61M 5/1723 604/504 |
| 2010/0174228 A1* | 7/2010 | Buckingham | ..... | A61M 5/142 604/66 |
| 2011/0021584 A1* | 1/2011 | Berggren | ..... | A61K 31/19 514/380 |
| 2012/0136336 A1* | 5/2012 | Mastrototaro | ..... | A61B 5/14532 604/504 |
| 2012/0203085 A1* | 8/2012 | Rebec | ..... | A61B 5/14532 600/310 |
| 2012/0225134 A1* | 9/2012 | Komorowski | ..... | A61K 33/24 424/655 |
| 2012/0232520 A1* | 9/2012 | Sloan | ..... | A61B 5/14532 604/504 |
| 2013/0158503 A1* | 6/2013 | Kanderian, Jr. | ..... | A61B 5/14532 604/504 |
| 2013/0261406 A1* | 10/2013 | Rebec | ..... | A61B 5/14532 600/301 |
| 2014/0121635 A1* | 5/2014 | Hayter | ..... | A61B 5/0031 604/504 |
| 2014/0180203 A1* | 6/2014 | Budiman | ..... | A61B 5/14532 604/66 |
| 2014/0278123 A1* | 9/2014 | Prodhom | ..... | A61M 5/1723 702/19 |
| 2015/0025329 A1* | 1/2015 | Amarasingham | ..... | G06F 19/3456 600/301 |
| 2015/0025495 A1* | 1/2015 | Peyser | ..... | A61B 5/14532 604/504 |
| 2015/0213217 A1* | 7/2015 | Amarasingham | ..... | G06F 19/3418 705/2 |
| 2016/0082187 A1* | 3/2016 | Schaible | ..... | A61B 5/14532 604/504 |
| 2017/0156682 A1* | 6/2017 | Doyle, III | ..... | A61B 5/746 |

OTHER PUBLICATIONS

Dassau et al., Real-Time Hypoglycemia Prediction Suite Using Continuous Glucose Monitoring, Diabetes Care, vol. 33, No. 6, Jun. 2010, p. 1249-54.

* cited by examiner

HEALTH MONITORING SYSTEM

CROSS REFERENCE TO RELATED APPLICATION

This application is a continuation of Ser. No. 13/166,806, filed: Jun. 22, 2011, which claims priority to Ser. No. 61/357,409, filed Jun. 22, 2010, the disclosure of which is incorporated herein by reference.

This work was supported by grant ROI-DK085628-01 from the National Institutes of Health; the Government has certain rights in this invention.

FIELD OF THE INVENTION

The field of the invention is a continuous glucose monitoring.

BACKGROUND OF THE INVENTION

Diabetes is a chronic disease only controlled by constant vigilance. Chronic elevations, and likely fluctuations, of the blood glucose may result in long term complications (blindness, kidney failure, heart disease, and lower extremity amputations). Perversely, attempts at normalizing glucose concentrations also increases the risk of serious health issues related to hypoglycemia. Despite the use of insulin infusion pumps and programs that promote intensive diabetes management, the average A1c (an indicator of long-term blood glucose control) reported by major diabetes treatment centers remains higher than 8%, well above the recommended goal of 6.5-7%. Many factors contribute to this failure:
1) the difficulties in correctly estimating the amount of carbohydrates in a meal,
2) missed meal boluses, and
3) anxiety about anticipated hypoglycemia, resulting in patients giving themselves less insulin, especially overnight.

It has always been difficult to achieve compliance with complicated medical regimens, such as the administration of insulin three or more times a day. As long as diabetes treatment demands constant direct intervention, the vast majority of people with diabetes will not meet treatment goals. An expanding area of research addressing diabetes is working on developing automated closed loop systems that integrates glucose readings and insulin delivery without the on-going active intervention of the patient—an "artificial pancreas".

We have developed an automated closed-loop system that contains a subcutaneous continuous glucose monitor and a subcutaneous insulin delivery pump for type 1 diabetes patients. These two components are connected by a control algorithm using data from the glucose sensor to determine the appropriate insulin delivery. We use a health monitoring system (HMS) algorithm that adds an independent safety layer to the overall system. The HMS analyzes CGM data and CGM trends in anticipation of impending hypoglycemia. The HMS issues electronic, visual and/or audio alerts in response to impending hypoglycemia (e.g. within 15 minutes), such as on the AP device screen, with a request for the investigator to intervene and treat the subject, e.g. with 16 g carbohydrate. A secondary alert may be sent as a text message, such as to the clinical team, that hypoglycemia is predicted and may also suggest taking outside action, such as eating carbohydrates, in order to prevent hypoglycemia.

RELEVANT LITERATURE

Dassau E., F. Cameron, H. Lee, B. W. Bequette, H. Zisser, L. Jovanovič, H. P. Chase, D. M. Wilson, B. A. Buckingham, and F. J. Doyle. Real-Time Hypoglycemia Prediction Suite Using Continuous Glucose Monitoring: A Safety Net for the Artificial Pancreas. Diabetes Care, 33(6):1249-1254, 2010.

Dunn T. C., R. C. Eastman, and J. A. Tamada. Rates of Glucose Change Measured by Blood Glucose Meter and the GlucoWatch Biographer During Day, Night, and Around Mealtimes. Diabetes Care, 27(9):2161-2165, 2004.

Seborg D. E., T. F. Edgar, D. A. Mellichamp, and F. J. Doyle III, Process Dynamics and Control, 3rd ed., Hoboken, N.J.: John Wiley & Sons, 2011.

Buckingham B, Cobry E, Clinton P, Gage V, Caswell K, Kunselman E, Cameron F, Chase H P. Preventing hypoglycemia using predictive alarm algorithms and insulin pump suspension. Diabetes Technol Ther 2009; 11:93-97

SUMMARY OF THE INVENTION

The invention provides computer-implemented algorithms, computers programmed with a subject algorithm, and methods and machines for processing continuous glucose monitoring (CGM) data and issuing an alert or negative feedback signal if hypoglycemia is imminent.

In one embodiment the invention provides a low glucose predictor and signal generator that uses a set of constraints to predict an imminent occurrence of hypoglycemia, comprising: (a) a pre-processing module that receives and modulates continuous glucose monitoring (CGM) data by reducing noise and adjusting for missed data points and shifts due to calibration; (b) a core algorithm module that receives data from the pre-processing module and calculates a rate of change to make a hypoglycemia prediction, and determine if hypoglycemia is imminent; and (c) an alarm mode module that receives data from the core algorithm and if hypoglycemia is imminent, issues an audio or visual alert or warning message or a negative feedback signal to an insulin delivery device.

In another embodiment of the invention provides a machine for processing continuous glucose monitoring (CGM) data and issuing an alert if hypoglycemia is imminent, the machine comprising a computer specifically programmed with: (a) a pre-processing module that receives and modulates continuous glucose monitoring (CGM) data by reducing noise and adjusting for missed data points and shifts due to calibration; (b) a core algorithm module that receives data from the pre-processing module and calculates a rate of change to make a hypoglycemia prediction, and determine if hypoglycemia is imminent; and (c) an alarm mode module that receives data from the core algorithm and issues an audio or visual alert or warning message or a negative feedback signal to an insulin delivery device if hypoglycemia is imminent.

In another embodiment the invention provides a low glucose predictor (LPG) core algorithm comprising a numerical logical algorithm that feeds a three-point calculated rate of change using backward difference approximation and the current glucose value into logical expressions to detect impending hypoglycemia, wherein the logical expressions verify that the rate of change is both negative and within a predetermined acceptable range as well as that the continuous glucose monitoring (CGM) glucose values are within predefined boundaries and that a pending hypoglycemic event is predicted within the threshold time window, and wherein the numerical logical algorithm provides tuning and insensitivity to sensor signal dropouts.

In another embodiment the invention provides a method of using a subject machine, programmed-computer or algorithm for processing continuous glucose monitoring (CGM) data and issuing an alert or signal if hypoglycemia is imminent, the method comprising the steps of: (a) receiving and modulating CGM data in a pre-processing module by reducing noise and adjusting for missed data points and shifts due to calibration; (b) receiving data from the pre-processing module in a core algorithm module that then calculates a rate of change to make a hypoglycemia prediction, and determine if hypoglycemia is imminent; and (c) receiving data from the core algorithm in an alarm mode module that then issues an audio or visual alert or warning message or a negative feedback signal to an insulin delivery device if hypoglycemia is imminent.

In particular embodiments of the subject inventions, in the preprocessing module the CGM data are filtered for noise using a noise spike filter to remove outliers and a low pass filter to damp electrical noise. To use the most current information, recently missed data points are interpolated using a simple linear interpolation. To prevent erroneous estimation of the rate of change when the sensor is calibrated, a calibration detection module is used: this detects a persistent offset in data and shifts the data from before the calibration accordingly. This module only operates when enough data is present to make a prediction (number of points required denoted as PR). If the number of points is less than PR or there are large gaps in the last PR points this module will not operate. This will operate during periods of sensor outage (up to two readings) by extrapolating previous estimates.

In particular embodiments of the subject inventions, in the core algorithm module the rate of change is estimated using the first derivative of the 3-point Lagrange interpolation polynomial. A series of logical steps is taken to ensure that the subject is within a reasonable proximity of the hypoglycemia threshold, the glucose is decreasing at a physiologically probable rate, and that the time to crossing the hypoglycemia threshold is within a preset prediction horizon. If these checkpoints are all passed, the alarm mode module is activated.

In particular embodiments of the subject inventions, in the alarm mode module when an imminent hypoglycemic event is predicted, the alarm mode references any previous alarms to ensure that it has been more than a pre-designated lockout period. This is to ensure that any action taken during the previous alarm has time to take effect. If this checkpoint is passed, an audible, electronic and visible alarm is issued. Methods of action may be any of the following: insulin delivery suspension, insulin delivery attenuation, or consumption of rescue carbohydrates.

Figure 2:
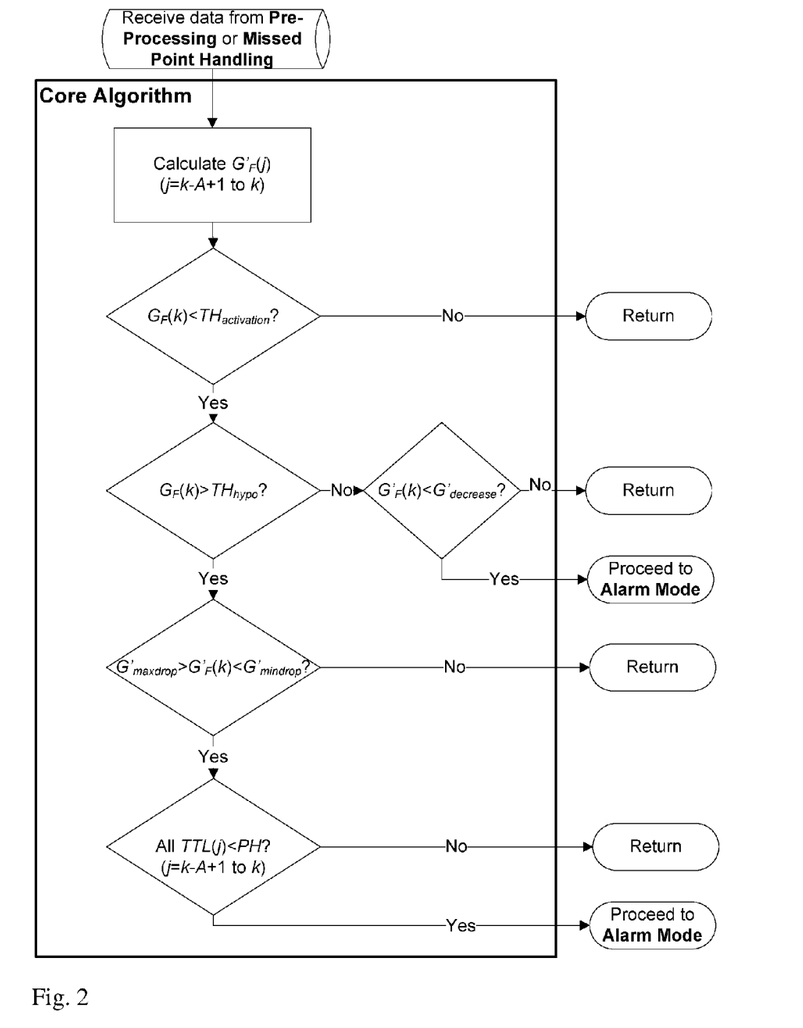
FIG. 2. Flow chart of the Core Algorithm module.

In another particular embodiment the preprocessing module implements the steps of FIGS. 1-1 and 1-2, the core algorithm module implements the steps of FIG. 2, and/or the alarm mode module implements the steps of FIG. 3-3.

In particular embodiments the subject inventions are operably-linked to an insulin delivery device and/or to a continuous glucose monitoring (CGM) device.

The invention provides all combinations of the recited particular embodiments as if each combination had been separately recited.

BRIEF DESCRIPTION OF THE DRAWINGS

FIG. 1-1. Flow chart of the Pre-Processing module.
FIG. 1-2. Flow chart of the Missed Point Handling section of the Pre-Processing module.
FIG. 3-1. Screenshot of the impending hypoglycemia pop-up window.
FIG. 3-2. Representation of the message when the CGM is below 70 mg/dL.
FIG. 3-3. Flow chart of the Alarm Mode module.

DETAILED DESCRIPTION OF SPECIFIC EMBODIMENTS OF THE INVENTION

The HMS functions as a process monitoring module that is executed in real time. This section of the control algorithm serves as a safety layer to the device. The zone-MPC algorithm controls the delivery of insulin, while the HMS evaluates the trend of the glucose in a different way in order to provide an extra layer of safety to ensure the health of the subject. The HMS will generate an audible and visual alert to the clinicians and send a text message to the physician in charge with a profile of the current trend and prediction for the upcoming 15 minutes. The key module of the HMS is the low glucose predictor (LGP) that uses a set of constraints to predict the imminent occurrence of hypoglycemia. The relevant variable is glucose concentration, G, assumed to be the CGM measurement. The LGP has three major modules: a pre-processing module to get the CGM data ready for prediction; a core algorithm section to calculate the rate of change, make predictions, and determine if hypoglycemia is imminent; and an alarm mode module to issue the audible and visual alert and send the warning text message.

The HMS can work with a control algorithm or without one, and any control algorithm can be used to deliver insulin. Insulin can be also delivered manually by the user. In addition, HMS parameters can be adjusted. e.g. PH 10-60 min, THactivation 90-150 mg/dL, THhypo 60-80 mg/dL, LT 15-45 min.

1. Pre-Processing

Figure 11:
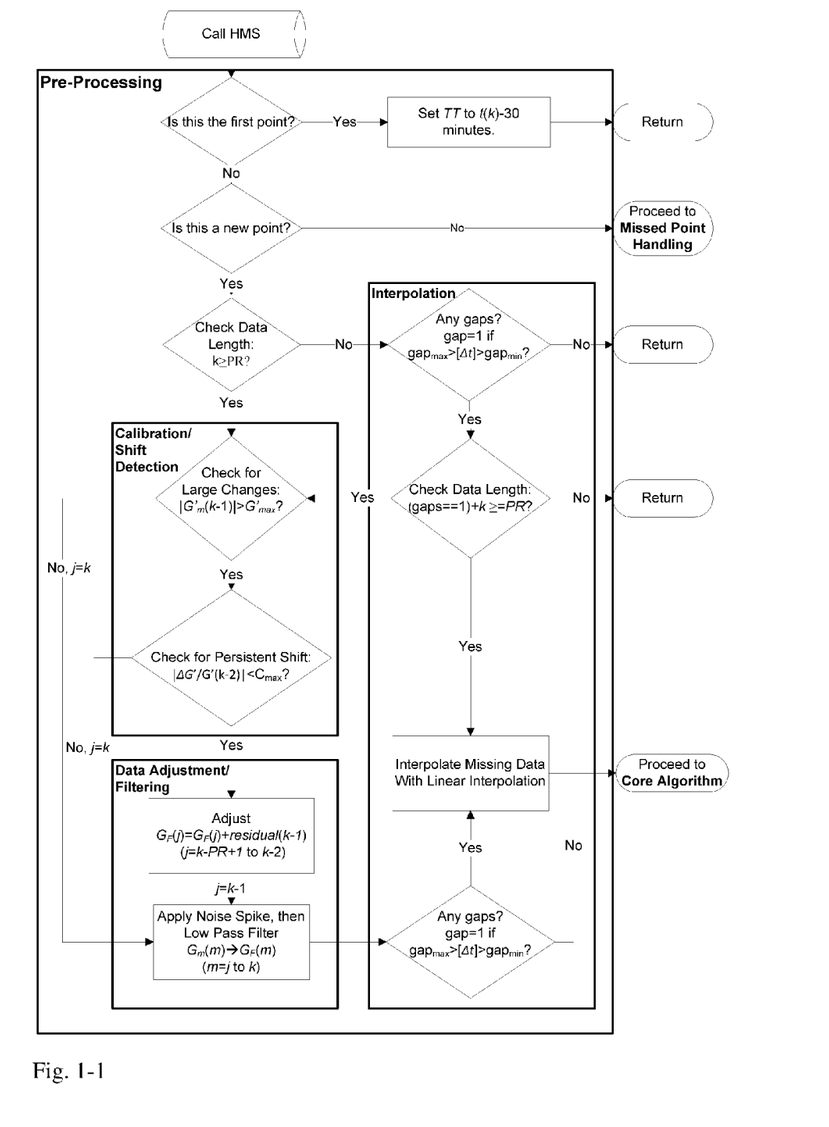

The pre-processing module is used to get the CGM data ready for prediction. The CGM often has noisy data, missed data points, and shifts due to calibration. These issues are all addressed in the pre-processing module. A flow diagram of the module can be seen in FIG. 1-1, with terms detailed in Table 1-1.

1.1 Missed Point Handling

Figure 12:
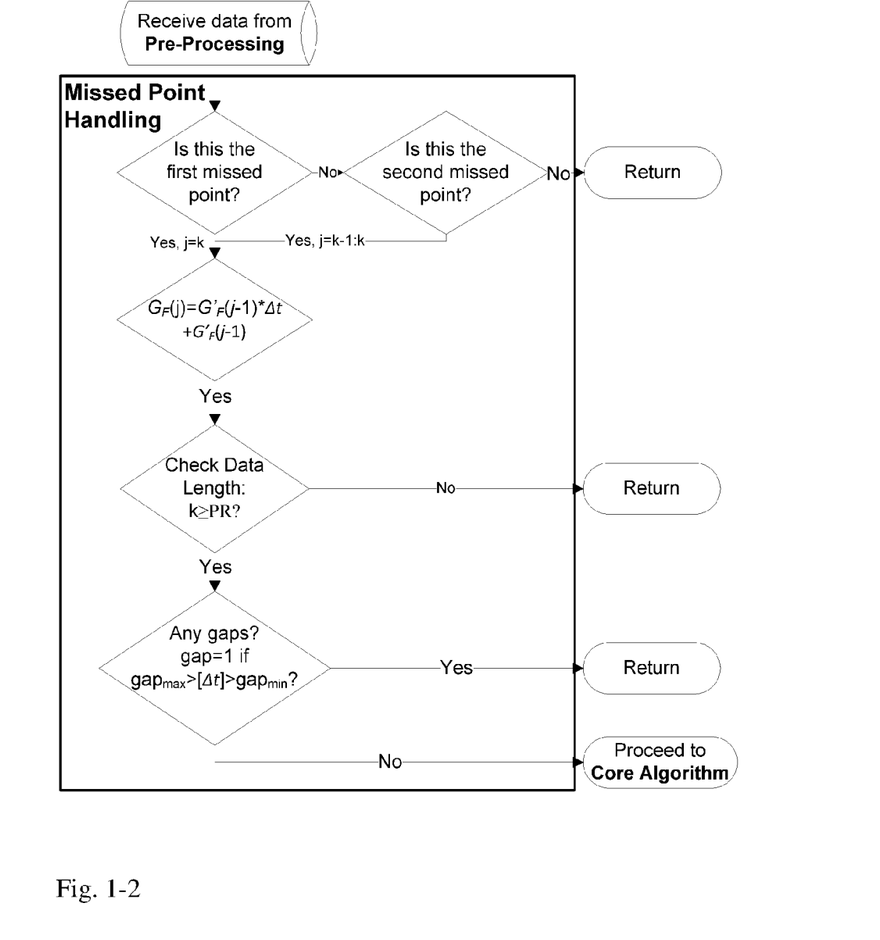

The HMS is called every five minutes regardless of missing data. To avoid missing a hypoglycemic event when G is low and falling and data is missing, the HMS will function when up to two points are missing. The estimation of the rate of change from the previous point is projected for the missing data (these data are not saved, only used for current hypoglycemia alarming if necessary). The HMS then proceeds directly to the Core Algorithm module using the predicted data as G(j) where j=k for one missed point and j=k-1, k for two missed points. Here, $G \in \mathbb{R}^{k \times 1}$. A flow diagram of this branch of the pre-processing module can be seen in FIG. 1-2.

1.2 Shift Detection

When the CGM is calibrated, a shift in the CGM data is introduced. In order to make a more accurate prediction, these shifts must be detected so that the shift does not produce a non-physiologic rate of change calculation. A shift in the signal is detected when the change in the raw signal is large (>4 mg/dL/min, considered to be non-physiologic) and then the next point continues roughly the same trend as before the shift, but with an offset (Dunn et al., 2004, supra).

When a shift is detected, the points after the shift can be considered to be more accurate, and the same offset can be applied to the points before the shift to reflect the true trend. If a shift is detected, the previous points are shifted as follows:

Shift detected if $\Delta G' < 0.5$ and $G_m'(k-1) > 4$ mg/dL/min where $$\Delta G' = \left| \frac{\frac{G_m(k) - G_m(k-1)}{t(k) - t(k-1)} - G_F'(k-2)}{G_F'(k-2)} \right|$$

and $$G_m'(k-1) = \left| \frac{G_m(k-1) - G_m(k-2)}{t(k-1) - t(k-2)} \right|.$$

$G_F$ is the filtered CGM data and $G'_F$ is the calculated rate of change. The calculations of $G_F$ and $G'_F$ are illustrated below in the data filtering and core algorithm sections, respectively. If a shift is detected, the previous points are shifted as follows:

$$G_F(j) = G_F(j) + \text{residual}(k-1)\ j = k-A-1:k-2$$

where A=number of subsequent alarms required to emit warning of hypoglycemia and $$\text{residual}(k-1) = G_m(k-1) - [G'_F(k-2) \times (t(k-1) - t(k-2)) + G_F(k-2)].$$

If a shift is detected, $G_F(k-1)$ is re-calculated using the updated $G_F$ vector.

1.3 Data Filtering

Due to electrical noise and interference, the CGM data is often noisy; hence filtering the data using physiologically-based parameters allows the data to more accurately reflect the blood glucose. The algorithm filters the data using a noise-spike filter to reduce the impact of noise spikes, derived as follows:

$$G_{F,NS}(k) = \begin{cases} G_m(k) & \text{if } |G_m(k) - G_F(k-1)| \leq \Delta G \\ G_F(k-1) - \Delta G & \text{if } (G_F(k-1) - G_m(k)) > \Delta G \\ G_F(k-1) + \Delta G & \text{if } (G_m(k) - G_F(k-1)) > \Delta G \end{cases}$$

where k is the sampling instant, $G_F(k-1)$ is the previous filtered value, $G_{F,NS}(k)$ is the filtered value resulting from the noise-spike filter, $G_m(k-1)$ is the measurement, and $\Delta G$ is the maximum allowable rate of change (Seborg, et al., 2011, supra). The data are then passed through a low pass filter to damp high frequency fluctuations from electrical noise, written as follows:

$$G_F(k) = \frac{\Delta t}{\tau_F + \Delta t} G_{F,NS}(k) + \left(1 + \frac{\Delta t}{\tau_F + \Delta t}\right) G_F(k-1),$$

where $\Delta t$ is the sampling time, $\tau_F$ is the filter time constant, and $G_F$ is the filtered value (Seborg et al., 2011, supra). A dimensionless parameter, $\alpha$, is defined as follows:

$$\alpha \Box \frac{\Delta t}{\tau_F + \Delta t},$$

and varies from 0 to 1 (0 not included), with the filtered value equaling the measurement if a equals 1, and the measurement being ignored as a approaches 0.

1.4 Interpolation

Dropped measurements can lead to missing data points. In order to allow the HMS to make a prediction even when points are missing, these points will be interpolated in order to allow a prediction to be made at that instance in time. The algorithm then interpolates gaps of up to 20 minutes using linear interpolation:

$$G_F(k - 1/2) = G_F(k-1) + (t(k-1/2) - (k-1)) \frac{(G_F(k) - G_F(k-1))}{(t(k) - t(k-1))},$$

where $G_F(k-\frac{1}{2})$ is the interpolated point, halfway between $t(k-1)$ and $t(k)$. Both the $G_F$ and t vectors are updated to include the interpolated point.

TABLE 1-1

Explanation of symbols in Missed Point Handling flow chart.

| Symbol | Value | Unit | Interpretation |
|---|---|---|---|
| A | 1 | — | Alarm Requirement: # of subsequent positive flags for alarm |
| Cmax | 0.5 | — | Maximum change: limits difference of G' before and after offset to detect shift |
| gap$_{max}$ | 20 | minutes | Maximum gap to interpolate. If this is exceeded, algorithm waits for enough points after the gap to predict. |
| gap$_{min}$ | 7 | minutes | Minimum gap to interpolate |
| G$_F$' | — | mg/dL/min | Estimated previous rate of change, used for missing point extrapolation. |
| G$_m$'(k − 1) | — | mg/dL/min | Slope of previous two points, used for shift determination. $G_m'(k-1) = \left\| \frac{G_m(k-1) - G_m(k-2)}{t(k-1) - t(k-2)} \right\|$ |
| G$_{max}$' | 4 | mg/dL/min | Maximum rate of change for shift detection |
| low pass filter | — | mg/dL | $G_F(k) = \frac{\Delta t}{\tau_F + \Delta t} G_{F,NS}(k) + \left(1 - \frac{\Delta t}{\tau_F + \Delta t}\right) G_F(k-1)$ |

TABLE 1-1-continued

Explanation of symbols in Missed Point Handling flow chart.

| Symbol | Value | Unit | Interpretation |
|---|---|---|---|
| noise spike filter | — | mg/dL | $G_{F,NS}(k) = \begin{cases} G_m(k) & \text{if } |G_m(k) - G_F(k-1)| \leq \Delta G \\ G_F(k-1) - \Delta G & \text{if } (G_F(k-1) - G_m(k)) > \Delta G \\ G_F(k-1) + \Delta G & \text{if } (G_m(k) - G_F(k-1)) > \Delta G \end{cases}$ |
| PR | 3 | — | A − 1 + order of the G' calculation |
| residual | — | mg/dL | Used to update previous points when shift is detected. residual(k − 1) = $G_m$(k − 1) − [$G_{F'}$(k − 2) × (t(k − 1) − t(k − 2)) + $G_F$(k − 2)] |
| TT | — | minutes | Last treatment time: used to determine it is too soon to alarm after previous alarm |
| ΔG | 3* Δt | mg/dL | Maximum allowable rate of change for the noise spike filter. |
| ΔG' | — | — | Used in shift detection to detect offset with similar rates of change before and after offset. $\Delta G' = \dfrac{\left| \dfrac{G_m(k) - G_m(k-1)}{t(k) - t(k-1)} - G'_F(k-2) \right|}{|G'_F(k-2)|}$ |
| $\tau_F$ | 3 | minutes | Filter time constant. |
| Δt | 5 | minutes | Sampling time: this may be longer if points are missing. |

2. Core Algorithm

In the core algorithm, the rate of change is calculated to make a prediction and issue an alarm if a hypoglycemic event is imminent. The rate of change is calculated and the trajectory is projected through the hypoglycemia threshold, TH, to decide if a hypoglycemic event will occur within the prediction horizon, PH. The rate of change calculation is as follows, using the first derivative of the Lagrange interpolation polynomial (Dassau et al., 2010, supra):

$$G'_F(j) \cong \frac{t(j) - t(j-1)}{(t(j-2) - t(j-1))(t(j-2) - t(j))} G_F(j-2) + \frac{t(j) - t(j-2)}{(t(j-1) - t(j-2))(t(j-1) - t(j))} G_F(j-1) + \frac{2t(j) - t(j-2) - t(j-1)}{(t(j) - t(j-1))(t(j) - t(j-2))} G_F(j)$$

where j=k−A+1:k. The following logic is then implemented:

if $G_F(k)$<70 mg/dL and $G'_F(k)$<−0.1 mg/dL/min, the Alarm Mode is activated else, if $G_F(k)$<110 mg/dL and −3 mg/dL/min<$G'_F(k)$<0 mg/dL/min and $$\frac{(TH - G_F(j))}{G'_F(j)} < PH \; \forall \; j = k - A + 1{:}k,$$

the Alarm Mode is activated

A flow diagram of the module can be seen in FIG. 2 (Flow chart of the Core Algorithm module, with terms detailed in Table 2-1.

TABLE 1-2

Explanation of symbols in Core Algorithm module flow chart.

| Symbol | Value | Unit | Interpolation |
|---|---|---|---|
| A | 1 | — | Alarm Requirement: # of subsequenct positive flags for alarm |
| $G_{decrease}'$ | −0.1 | mg/dL/min | Decreasing G': cutoff used when G is below $TH_{hypo}$ to determine if the trend is negative. |
| $G_F'$ | — | mg/dL/min | Estimated current rate of change, using Lagrange interpolation polynomials. $G'_F(j) \cong \dfrac{t(j) - t(j-1)}{(t(j-2) - t(j-1))(t(j-2) - t(j))} G_F(j-2) - \dfrac{t(j) - t(j-2)}{(t(j-1) - t(j-2))(t(j-1) - t(j))} G_F(j-1) + \dfrac{2t(j) - t(j-2) - t(j-1)}{(t(j) - t(j-1))(t(j) - t(j-2))} G_F(j)$ |
| $G_{maxdrop}'$ | −3 | mg/dL/min | Maximum drop of G: cutoff used for alarming. If drop is greater than this, it is considering non-physiologic and will not alarm. |
| $G_{mindrop}'$ | −0.5 | mg/dL/min | Minimum drop of G: cutoff used for alarming. If G is not dropping, hypoglycemia is not imminent. |
| PH | 15 | minutes | Prediction Horizon: time through which the prediction is projected. |
| $TH_{activation}$ | 110 | mg/dL | Activation threshold: alarm can only be triggered when G is below this threshold to focus on danger of imminent hypoglycemia. |
| $TH_{hypo}$ | 70 | mg/dL | Hypoglycemia threshold: prediction is compared against this to determine danger of imminent hypoglycemia. |

TABLE 1-2-continued

Explanation of symbols in Core Algorithm module flow chart.

| Symbol | Value | Unit | Interpolation |
|---|---|---|---|
| TTL | — | minutes | Projected time to crossing $TH_{hypo}$. $TTL(j) = \frac{(TH - G_F(j))}{G'_F(j)}$ |

Alarm Mode

Figure 31:
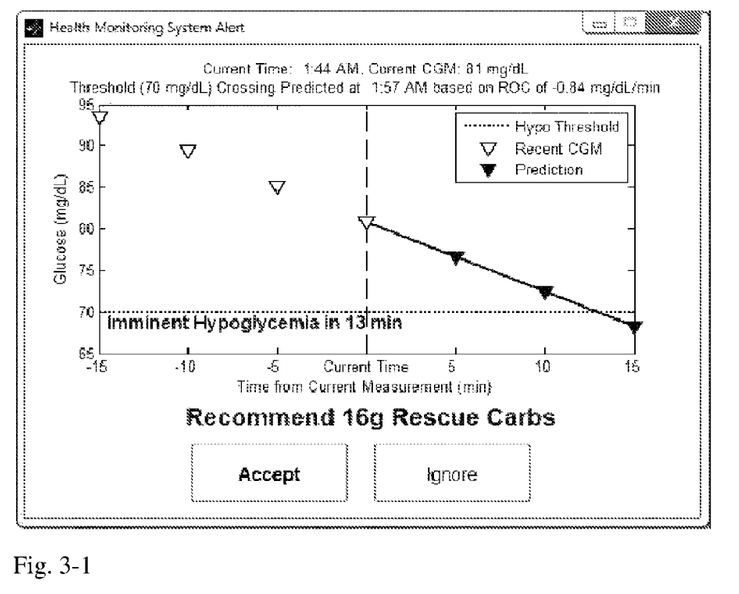

The alarm mode will issue an audible and visible alarm and activate E911, sending a short message service (SMS) to the attending physician. If any alarms have been issued and acknowledged in the past 30 minutes, no alarm is issued. If not, a version of the following message will pop up for predicted hypoglycemia, informing the clinicians of impending hypoglycemia, the current rate of fall, and the time to predicted low; see, FIG. 3-1 for screenshot of the impending hypoglycemia pop-up window.

Figure 32:
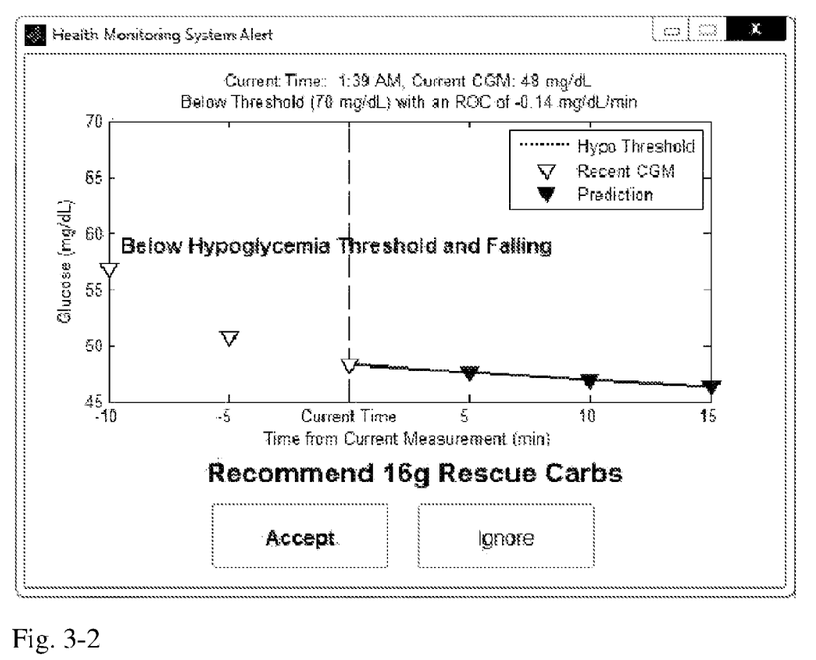
Figure 33:
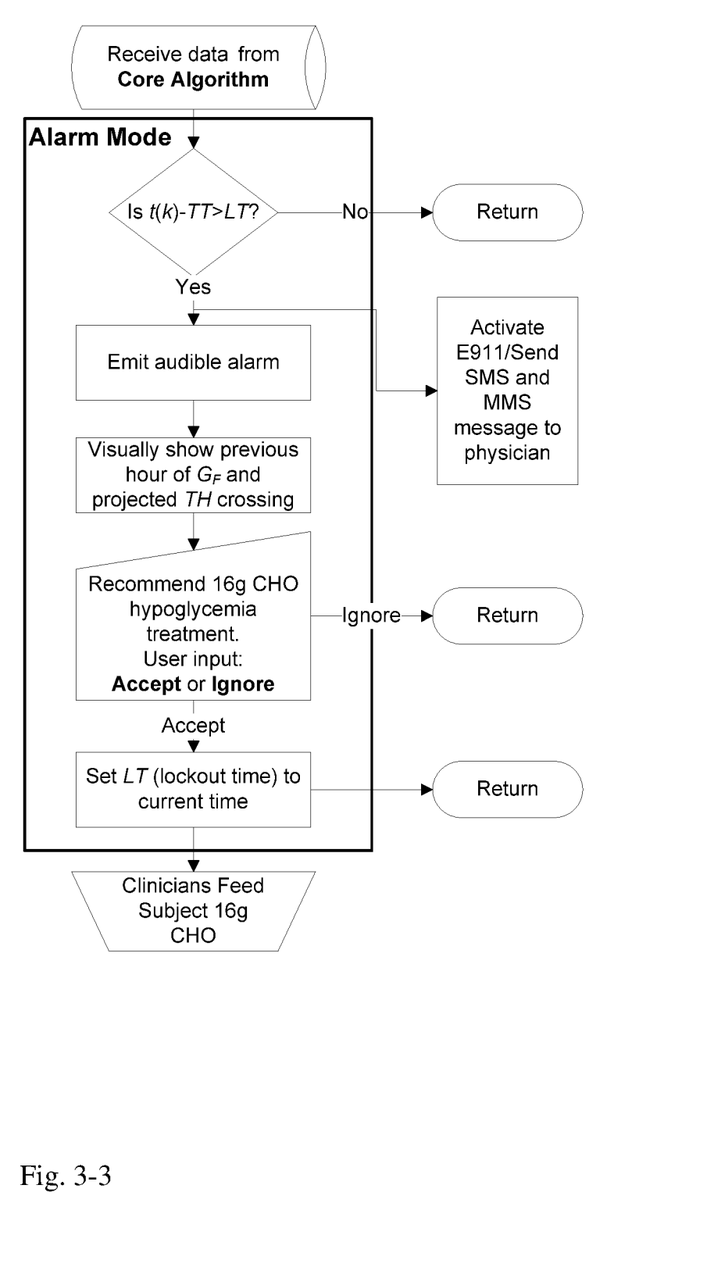

Data from user input (Accept or Ignore) will go to the algorithm for use as a lockout window before subsequent alarms. Should they accept, clinicians will then administer 16 g of rescue carbohydrates to the subject. Also, if the threshold has been crossed without alarms occurring and the CGM values continue to fall, a version of the message of FIG. 3-2 (Representation of the message when the CGM is below 70 mg/dL) will appear.

These figures will also be sent in a multimedia messaging service (MMS) to the physician in charge. This adds redundancy to ensure that treatment is given. A flow diagram of the module can be seen in FIG. 3-2 with terms detailed in Table 3-1.

TABLE 3-1

Explanation of symbols in Alarm Mode module flow chart.

| Symbol | Value | Unit | Interpretation |
|---|---|---|---|
| $TH_{hypo}$ | 70 | mg/dL | Hypoglycemia threshold: prediction is compared against this to determine danger of imminent hypoglycemia. |
| TT | — | minutes | Last treatment time: used to determine it is too soon to alarm after previous alarm |
| LT | 30 | minutes | Treatment lockout time: minimum time allowed between alarms |

In a particular embodiment the disclosed Health Monitoring System (HMS) is adapted for us in conjunction with an Artificial Pancreas (AP) Device for type 1 diabetes (T1DM) patients using a model-predictive control (MPC) algorithm (or MPC, PID, PD, FL, NMPC, etc.) with a subcutaneous insulin delivery pump and a subcutaneous continuous glucose monitor.

Figure 4:
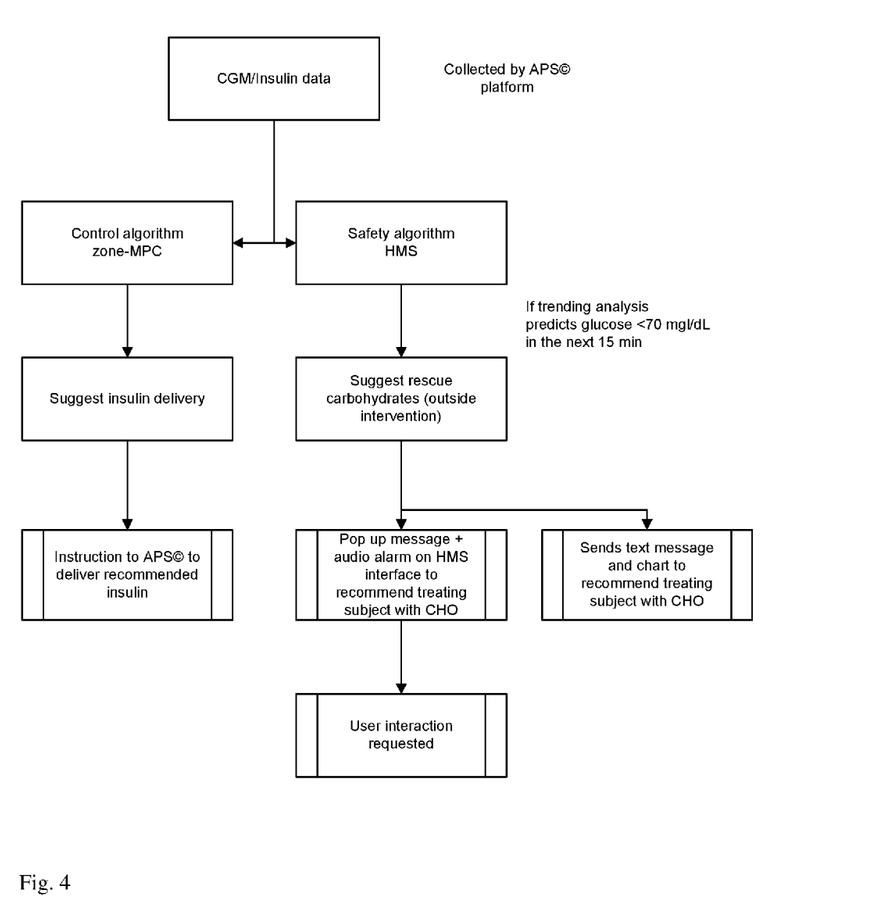
FIG. 4. Control algorithms overview.

The AP device is composed of the Artificial Pancreas System platform (APS©) developed by the University of California, Santa Barbara (UCSB) and Sansum Diabetes Research Institute (SDRI). The APS© is the current leading research platform used in this arena. It has been safely used in over 100 individual clinical sessions at eight leading clinical research centers around the world. This AP device is a closed-loop insulin pump/continuous glucose monitor (CGM) system regulated by a proprietary control algorithm, and comprises:

(1) Artificial Pancreas System (APS©) platform (version 0.3.0) documented in MAF-1625 including the following insulin pump and CGM:

OneTouch@ Ping® Glucose Management System by Animas Corporation (K080639 and MAF-1777). It is also called a Continuous Subcutaneous Insulin Infusion (CSII) pump; and DexCom™SEVEN☐PLUS by DexCom™ Corporation (P050012 and MAF-1564);

Interface to connect these components is programmed in MATLAB® language (revision 2009b);

Accessory hardware to connect the components together;

(2) Control algorithms including the following components (FIG. 4):

a zone Model Predictive Control (zone-MPC) algorithm that automatically regulates the rate of insulin delivery based on the glucose level of the patient, historical glucose measurement and anticipated future glucose trends, and patient specific information; and a Health Monitoring System (HMS) algorithm that adds an independent safety layer to the overall system. The HMS analyzes CGM data and CGM trends in anticipation of impending hypoglycemia. The HMS issues electronic, visual and/or audio alerts in response to impending hypoglycemia (e.g. within 15 minutes), such as on the AP device screen, with a request for the investigator to intervene and treat the subject, e.g. with 16 g carbohydrate. A secondary alert may be sent as a text message, such as to the clinical team, that hypoglycemia is predicted and may also suggest taking outside action, such as eating carbohydrates, in order to prevent hypoglycemia. For example, the HMS will send a warning message when predicting that glucose level by CGM will be <70 mg/dL in the following 15 minutes, and the visual and audio alarms appear on the AP device screen as shown by FIG. 3-1.

A secondary redundant alert is also sent via text graph to the clinical team. The text can be received on any cell phone, while the added graph (MMS) message with the chart can only be received on "smart phones". The text and graphic messages indicate that hypoglycemia is predicted within the next 15 minutes (or less) and recommend taking outside intervention to prevent predicted hypoglycemia and treat the subject with carbohydrates. The SMS and MMS messages are redundant alerts to the audio and visual alerts on the AP device screen. The visual pop-up window on the AP device computer interface must be acknowledged.

If the investigator selects the "ignore" button of the HMS warning, at the next cycle, i.e. 5 minutes later, if the prediction is that glucose concentration is predicted to be <70 mg/dL in the following 15 minutes, a new alarm will sound and appear.

If the investigator selects the "accept" button and the subjects is treated with carbohydrates as recommended, the system will perform a new analysis at the next cycle, but the alarm will not be activated for 30 minutes. If after 30 minutes the prediction is for a risk of hypoglycemia (<70 mg/dL), then a new alarm will occur. If the ingestion of carbohydrates prevented hypoglycemia, then, no alarm will occur.

Figure 5:
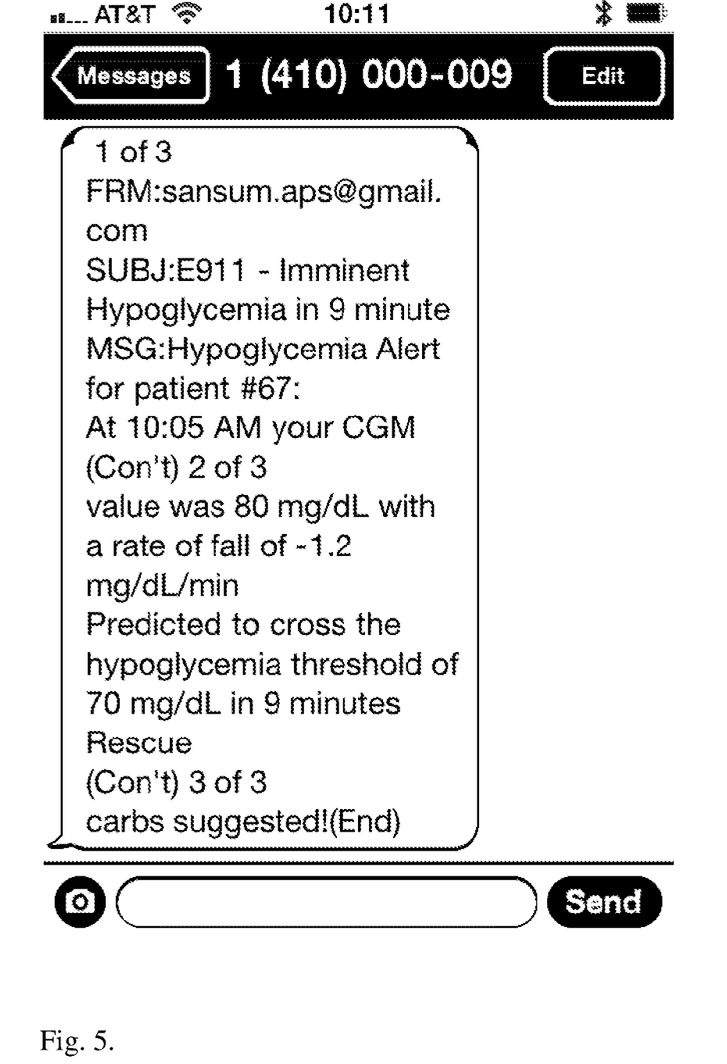
FIG. 5. Text message view to inform of predicted hypoglycemia

FIG. 5 show an example of the text message that is sent to the clinician. The same text message can be sent to any cell phone, and if the phone is a "smart phone", it will also receive the trending visual plot of the glucose level and its prediction trend.

Real-time prediction of pending adverse events by the Health Monitoring System (HMS) allows prevention by either a corrective action or shifting to manual control. This invention is based on CGM data that provides a reliable layer of protection to insulin therapy.

The first module in the HMS is a real-time hypoglycemia prediction algorithm that includes a projection based on a short term linear extrapolation of the glucose profile. This algorithm first processes the data using a filter, interpolation of missed points, and calibration detection. The risk of imminent hypoglycemia is then calculated, and, if warranted, an audible and visual alarm is sounded. In addition, the information about the current state of the system and the prediction of hypoglycemia is sent to the physician in charge via SMS and MMS. The mitigation of this event is to consume 16 g of carbohydrate, which should minimize the risk of severe hypoglycemia.

The systems and methods of the disclosure can be implemented in a computer or processor operably-associated with continuous glucose monitoring (CGM) devise and/or an insulin diabetes system or pump. The HMS may incorporate a hypoglycemia prediction algorithm (HPA) such as disclosed in U.S. Ser. No. 61/357,409, filed Jun. 22, 2010, and the core algorithm may embody a numerical logical algorithm that feeds a three-point calculated rate of change using backward difference approximation and the current glucose value into logical expressions to detect impending hypoglycemia. The logical expressions verify that the rate of change is both negative and within an acceptable range as well as that the CGM glucose values are within predefined boundaries and that a pending hypoglycemic event is predicted within the threshold time window. Numerical logical algorithm provides insensitivity to sensor signal dropouts and easy tuning.

In one aspect the invention effectively transforms CGM data into a physicality that is an audio and/or visual alert that hypoglycemia is imminent. In another aspect the invention effectively transforms CGM data into a negative feedback signal and send it to an insulin delivery device, which consequently actuates the delivery device, such as by restricting fluid flow, adjusting a fluid valve, reducing or shutting off a pump, etc.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of continuous glucose monitoring (CGM), comprising:
    processing the CGM data with a control algorithm to determine an appropriate insulin delivery and direct an insulin pump to make the delivery; and
    executing a health monitoring system (HMS) comprising steps:
    (a) calculating a rate of change of glucose concentration of the person based on the CGM data;
    (b) determining that a hypoglycemia condition is expected to occur based on the CGM data and the calculated rate of change of the glucose concentration of the person; and
    (c) issuing an alert prompting the person to take an action to avoid the hypoglycemia condition, wherein the action comprises consuming carbohydrates,
    wherein the HMS functions as a process monitoring module executed in real time, and the control algorithm and HMS evaluate the CGM data differently to provide an extra safety layer;
    wherein determining that the hypoglycemia condition is expected to occur comprises comparing the glucose concentration data to a first adjustable threshold and comparing the rate of change of the glucose concentration to a second adjustable threshold, and determining that the hypoglycemia condition is expected to occur within an adjustable time window.

2. The method of claim 1, wherein the alert is an electronic, visual and/or audio alert prompting the person to consume the carbohydrates.

3. The method of claim 1, wherein the alert is sent to a cellular phone.

4. The method of claim 2, wherein the alert is sent to a cellular phone.

5. A system for continuous glucose monitoring (CGM) of a diabetic person, comprising:
    a CGM device;
    an insulin delivery pump;
    a pump controller configured with a control algorithm to use data from the CGM device to determine an appropriate insulin delivery and direct the insulin delivery pump to make the delivery; and
    a health monitoring system (HMS) comprising a processor configured to execute an HMS algorithm using the CGM data to calculate a rate of change of glucose concentration of the person and determine that a hypoglycemia condition is expected to occur based on the CGM data and the calculated rate of change of the glucose concentration of the person; and a signal generator configured to generate an electronic, visual and/or audio alert in response to the impending hypoglycemia condition prompting the user to take an action to avoid the hypoglycemia condition, wherein the action comprises consuming carbohydrates,
    wherein the HMS functions as a process monitoring module executed in real time, and the control algorithm and HMS evaluate the CGM data differently to provide an extra safety layer;
    wherein the HMS algorithm compares the glucose concentration data to a first adjustable threshold, and compares the rate of change of the glucose concentration to a second adjustable threshold, and determines that the hypoglycemia condition is expected to occur within an adjustable time window.

* * * * *